United States Patent
Chung et al.

(10) Patent No.: US 7,357,933 B2
(45) Date of Patent: Apr. 15, 2008

(54) SPORODERM-BROKEN GERMINATION-ACTIVATED GANODERMA LUCIDUM SPORES FOR PROTECTION OF DOPAMINERGIC NEURONS AND TREATMENT OF PARKINSON'S DISEASE

(75) Inventors: Chee-Keung Chung, Kowloon (HK); Zhou Lin Liu, Guangzhou (CN)

(73) Assignee: Enhan Technology Holdings International Co., Ltd., Kowloon (HK)

( * ) Notice: Subject to any disclaimer, the term of this patent is extended or adjusted under 35 U.S.C. 154(b) by 292 days.

(21) Appl. No.: 11/121,985

(22) Filed: May 5, 2005

(65) Prior Publication Data

US 2005/0249751 A1     Nov. 10, 2005

Related U.S. Application Data

(60) Provisional application No. 60/567,779, filed on May 5, 2004.

(51) Int. Cl.
*A01N 65/00*     (2006.01)
(52) U.S. Cl. .................................. 424/195.15
(58) Field of Classification Search ..................... None
See application file for complete search history.

(56) References Cited

U.S. PATENT DOCUMENTS 6,464,982 B1 * 10/2002 Lam ...................... 424/195.15
2004/0146591 A1 * 7/2004 Wang ........................ 424/769

FOREIGN PATENT DOCUMENTS

CN    1111529    * 11/1975

OTHER PUBLICATIONS

Cheung et al. FEBS Letters. 2000. vol. 486, pp. 291-296.*
Emborg, M. J. Neurosci. Methods. 2004. vol. 139, pp. 121-143.*
Zhao et al. J. Pharmacol. Sci. 2004. vol. 95, pp. 294-298.*
Wang et al. Chinese J. Clin. Rehab. 2005. vol. 9, No. 48, pp. 71-73, Embase Abstract enclosed.*
Xie et al. Chinese J. Neurol. 2005. vol. 38, No. 6, pp. 355-358, Embase Abstract enclosed.*
Zhu et al. Academic J. of the First Meical College of PLA. 2005. vol. 25, No. 6, pp. 667-671, Medline Abstract enclosed.*
Ma et al. Jiepiou Xuebao. 2005. vol. 36, No. 6, pp. 597-603, Biosis Abstract enclosed.*

* cited by examiner

*Primary Examiner*—Christopher R. Tate
(74) *Attorney, Agent, or Firm*—Fei-Fei Chao; Andrews Kurth LLP (57) ABSTRACT

This invention provides a method for treating Parkinson's disease (PD), particularly early stage of PD by orally administering to a mammal sporoderm-broken germination activated *Ganoderma lucidum* spore powders (GASP) to reduce and/or release the symptom of rotatory behavior in PD, to reduce the progression of neuron apoptosis and to improve the tyrosine hydroxylase (TH) activity so as to increase the conversion of hydroxydopamine (DOPA) to dopamine in the dopaminergic neurons. This invention also provides a method for reducing neuron apoptosis and a method for improving TH activity in dopaminergic neurons by orally administering to a mammal GASP.

21 Claims, 8 Drawing Sheets

SPORODERM-BROKEN GERMINATION-ACTIVATED GANODERMA LUCIDUM SPORES FOR PROTECTION OF DOPAMINERGIC NEURONS AND TREATMENT OF PARKINSON'S DISEASE

RELATED APPLICATION

This application claims the priority of U.S. Provisional Patent Application Ser. No. 60/567,779, filed on May 5, 2004, which is herein incorporated by reference.

FIELD OF THE INVENTION

This invention relates to a method for treating Parkinson's disease (PD), particularly early stage of PD by administering, preferably orally administering, to a mammal sporoderm-broken germination activated *Ganoderma lucidum* spore powders (GASP). GASP reduces and/or releases the symptom of rotatory behavior in PD, reduces the progression of neuron apoptosis, improves the tyrosine hydroxylase (TH) activity, particularly by increasing the conversion of hydroxydopamine (DOPA) to dopamine in the dopaminergic neurons in the substantia nigra region of the midbrain. This invention also relates to a method for reducing neuron apoptosis and a method for improving TH activity in dopaminergic neurons by administering, preferably orally administering, to a mammal GASP.

BACKGROUND OF THE INVENTION

Parkinson's Disease is a chronic central nervous system disorder characterized by a disturbance of voluntary movement in which muscles become stiff and sluggish, movement becomes clumsy and difficult, and uncontrollable rhythmic twitching of groups of muscles produces characteristic shaking or tremor. At the present time, approximately 1.5 million Americans are diagnosed with Parkinson's Disease. The condition of Parkinson's Disease is believed to be caused by a degeneration of pre-synaptic dopaminergic neurons in the central nervous system, possibly in the substantia nigra region of the brain, due to absence of adequate release of a chemical transmitter, dopamine ("DA"), during neuronal activity. DA is partly responsible for starting a circuit of messages that coordinate normal movement of the body.

In the neurons, DA is produced by decarboxylation of 3,4-dihydroxyphenylalanine ("DOPA"), the immediate precursor of dopamine (DA). DOPA in turn is produced by hydroxylation of tyrosine. The enzyme tyrosine hydroxylase (TH) catalyzes the rate-limiting step of converting tyrosine to DOPA. The activity of TH in the peripheral and central nervous system is subject to short and long term regulation by extra- and intracellular signals. Such signalling provides the mechanisms for modulation of the amount of DA (as well as norepinephrine and epinephrine) synthesized and available for secretion in response to physiological requirements.

Recent studies, which were based on examination of postmortem brains from Parkinson's Disease patients and animal models, have suggested that at least a part of the neuron loss is due to apoptosis, a genetically programmed cell suicidal program. (Anglade et al. *Histol. Histopathol.* 1997; 12(1):25-31).

Apoptosis, or programmed cell death, is a principal mechanism by which organisms eliminate unwanted cells. Normal tissues in the body are formed either by cells that have reached a terminally differentiated state and no longer divide or by cells that die after a period of time and are replaced from a pool of dividing cells. For example, nervous tissue is formed early in development and the cells of the nervous system reach a terminally differentiated state soon after birth. When nervous tissue is damaged, the nerve cells are incapable of dividing and, therefore, the loss of function due to the damaged nerve cells is not repaired. The deregulation of apoptosis, either excessive apoptosis or the failure to undergo it, has been implicated in a number of diseases such as cancer, acute inflammatory and autoimmune disorders, ischemic diseases and certain neurodegenerative disorders, including Parkinson's Disease.

During apoptosis, a range of cellular molecules are inappropriately activated and subsequently destroy the cell. In mammals, the central execution molecules for apoptosis are a group of enzyme called caspases. Among the 14 caspases identified so far, caspase 3 appears to play a central role in the final execution of cell death. Upon activation, caspase 3 cleaves a variety of essential cytoplasmic and nuclear proteins, ensuring the inevitability of cell death. (Dodel et al. *Brain Res. Mol. Brain Res.* 1999; 64(1):141-148; Schierle et al. *Nat. Med.* 1999; 5(1):97-100; Hartmann et al. *PNAS* 2000; 97(6):2875-2880; Anantharam et al. *J. Neurosci.* 2002; 22(5):1738-1751).

As a result of the dopaminergic neuron death, the neurons in the next part of basal ganglia called striatum are not adequately stimulated, resulting in the symptoms of PD. At the cellular level, round protein aggregates called Lewy bodies are seen in the damaged and dying neurons of the substantia nigra. The first symptoms of PD do not appear until there are substantial loss (about 50%) of neurons in the substantia nigra and more than 80% reduction in dopamine levels. The classic trio of primary symptoms of PD is tremor at rest, rigidity (stiffness) and bradykinesia (slow movement).

Currently, there is no curative treatment for PD. There is no medication that slows or stops the progression of PD either. Currently available medications for PD are symptomatic therapies that suppress or reduce the symptoms of PD.

Levodopa is the most effective treatment currently available for the symptoms of PD. Most PD patients will eventually be on levodopa treatment. Carbidopa is frequently given together with levodopa to prevent its conversion in the intestine and blood, reducing the side effects of levodopa (nausea and vomiting) and increasing the amounts of levodopa available to the brain. However, after years of levodopa treatment, there may be a "wearing-off" of its beneficial effects. PD patients may experience "end of dose failure", that is, patients may feel good ("on") for a period of time and then the PD symptoms return ("off") before the next dose is taken. This on-off phenomenon is difficult to treat. In addition, patients may experience dyskinesias at an overdosage or peak-dose of levodopa. That is, patients may have abnormal involuntary movements with irregular, flowing, dance-like or jerky motion in any or all parts of the body.

Other symptomatic treatments of PD includes anticholinergics (e.g., trihexyphenidyl, benztropine, and biperiden), monoamine oxidase inhibitor (MOI, e.g., selegiline), dopamine receptor agonists (e.g., pergolide, bromocriptine, pramipexole and ropinirole), amantadine, catechol-o-methyltransferase (COMT) inhibitors (e.g., tolcapone and entacapone), and less frequently, some beta-blockers. Uses of these symptomatic agents involve side effects such as dry mouth, decreases memory, confusion, blurred vision, difficulty with urination, worsening constipation, sleep problems, nausea, nightmares, hallucinations, benign skin discoloration, liver damage (i.e., tolcapone), low blood pressure, slow heart rate and depression, etc.

In short, there remains the great demand for a medication that stops or slows the progression of PD while in the meantime causes fewer side effects.

In investigating PD and searching for a treatment, toxin-induced and genetic experimental models have been invaluable. The most established method is the treatment of animals with toxins that are specific for dopamine neurons, e.g., 6-hydroxydopamine (6-OHDA) and 1-methyl-4-phenyl-1,2,3,6-tetrahydropyridine (MPTP). After injection into an animal, these toxins are transported into dopaminergic neurons by selective uptake systems. These toxins concentrate in the neurons and eventually cause cell death, reproducing many characteristic features of PD. Both 6-OHDA and MPTP can replicate the neurochemical, morphologic, and behavioral changes seen in human disease (Tolwani et al. *Laboratory Animal Science* 1999; 49(4):363-371). These animal PD models are useful for studying many aspects of the PD and the effects of new treatments.

The rat is most commonly used for the 6-OHDA PD model due to established stereotactic techniques and reasonable cost. Typically, only one hemisphere is injected, introducing a unilateral lesion leading to asymmetric motor behavior. The asymmetric motor behaviors, such as circling behavior, result from a physiological imbalance between the lesioned and intact sides. About 1 week after injection, the dopamine pools on the lesioned side are depleted and lead to up-regulation and hypersensitivity of the dopamine receptors on the lesioned side. When the animals are challenged with apomorphine, a dopamine receptor agonist, the stimulation of these up-regulated receptors leads to contralateral circling (away from the lesioned side). The circling behavior can be quantified and used to access the efficacy of potential PD therapeutic agents. In addition, presence of the dopamine-producing neurons in the brain tissue can be identified by immunohistochemistry and Western blot of tyrosine hydroxylase in the brain tissues, and by in situ hybridization of the tyrosine hydroxylase mRNA in the neurons. Furthermore, detection of apoptotic dopaminergic cells can be carried out by immunohistochemistry and Western blot of caspase 3 in the brain tissues, and by in situ hybridization of the caspase 3 mRNA in the neurons. The techniques of immunohistochemistry, Western blot, and in situ hybridization are well known in the art.

Currently, the most widely used treatment for Parkinsonism is administration of L-DOPA, a precursor of dopamine which acts indirectly by replacing the missing dopamine. However, disadvantages are associated with the use of L-DOPA, for example, patients often suffer from side-effects such as dyskinesia and on-off effects, and it is necessary to administer L-DOPA in conjunction with a peripheral dopa-decarboxylase inhibitor such as carbidopa or benzaseride. These inhibitors prevent the peripheral degradation of levodopa to dopamine, thus enabling more drug to enter the brain and limiting peripheral side-effects. Such treatment improves quality of life for patients but does not halt disease progression. Furthermore, such treatment is associated with a number of adverse effects including nausea, vomiting, abdominal distension and psychiatric side-effects (for example, toxic confusional states, paranoia and hallucinations).

An alternative form of therapy is to administer postsynaptic dopamine agonists, for example ergot alkaloids such as bromocriptine—however, this approach is also associated with side-effects. For example, patients receiving bromocriptine often experience dyskinesia psychiatric problems, and in a small number of cases experience vasopastic phenomena and angina. Bromocriptine also causes psychiatric side-effects such as hallucinations. Thus, there is a continuing need for finding an effective and safe medicaments to treat patients with Parkinson disease.

In the invention to be presented in the following sections, a novel use of sporoderm-broken germination-activated *Ganoderma* spores (GASP) from *Ganoderma lucidum* as an effective, safe and practical alternative to prevent or treat Parkinson's Disease is described. The GASP has previously been disclosed for use in treating patients with cancer, AIDS, hepatitis, diabetes, cardiovascular diseases and spinal cord injury, and can prevent or inhibit free radical oxidation and hepatotoxic effects. See U.S. Pat. Nos. 6,316,002 and 6,468,542, which are incorporated herein by reference. To date, however, there have been no reports on the effects of GASP on Parkinson's Disease. A further benefit of using the GASP is that they are non-toxic so that higher dosage can be prescribed to the patients.

SUMMARY OF THE INVENTION

One objective of the present invention is to provide a method for treatment of Parkinson's disease (PD) in a mammal by administering an effective amount of germination activated *Ganoderma lucidum* spores (GASP). The preferred mammal is human. The antiparkinsonian effect of GASP is resulted from the protective ability of GASP on brain tissues, particularly neurons in the substantia nigra region. In particular, GASP improves tyrosine hydrolase (TH) activity in neurons by increasing the conversion of hydroxydopamine to dopamine.

Although the exact mechanism of action of GASP is unknown, it is proven by the inventors of the present invention that administration of GASP to a mammal having PD slow or stop the progression of neuron apoptosis in PD, particularly at an early stage of PD, such as by reducing and/or releasing the symptom of rotatory behavior. In some mammals, the progression of PD is even reversed.

GASP are preferred to be orally administered to the mammals. Due to the non-toxic characteristics of GASP, the effective amount of GASP given to a mammal is about 0.5 to 15 g per kg per day, preferably about 1 and 8 g per kg per day, and most favorably about 5 g per kg per day, to treat mammals with PD during the early stage of the disease.

Another objective of the present invention is to provide a method for protecting dopaminergic neurons from neuron apoptosis in a mammal, preferably a human, by administering, preferably orally administering, to the mammal an effective amount of germination activated *Ganoderma lucidum* spore powders (GASP) by increasing the tyrosine hydroxylase (TH) activity by converting hydroxydopamine to dopamine in the dopaminergic neurons, particularly in substantia nigra regiono of the midbrain.

Finally, the present invention provides a method for increasing tyrosine hydroxylase activity by converting hydroxydopamine to dopamine in dopaminergic neurons of a mammal by administering, preferably orally administering, to said mammal, preferably a human, an effective amount of germination activated *Ganoderma lucidum* spore powders (GASP).

BRIEF DESCRIPTION OF DRAWINGS

FIG. 7). There is a marked increase in the numbers of TH positive cells in the GASP treatment group when comparing to the PD model control group (FIG. 9 vs. FIG. 8).

FIG. 10). There is a marked decrease in the numbers of caspase 3 positive cells in the GASP treatment group when comparing to the PD model control group (FIG. 12 vs. FIG. 11).

DETAILED DESCRIPTION OF THE INVENTION

The present invention provides a method for providing neuroprotection of dopaminergic neurons and treatment of Parkinson's Disease (PD). The method involves administering an effective amount of germination activated *Ganoderma* spore powders (GASP) into a mammal having PD.

*Ganoderma* (*Ganoderma lucidum* Leyss ex Fr. Karst) is a polyporous fungus which belongs to the class Basidiomycetes, the family Polypolaceae, and the genus *Ganoderma*. *Ganoderma* spores are tiny and mist-like spores of 5~8 µm in sizes which have extremely hard and resilient, double-layer epispores, thus making them difficult to break open. The spores contain high concentrations of many bioactive substances, including, but are not limited to, polyunsaturated fatty acids, polysaccharides, vitamins, sterols, trace minerals, amino acids, and triterpenes. The GASP used in the present invention are sporoderm-broken (i.e., the double-layer epispores of the spores are broken so that the bioactive substances within the spores are released), which is produced by the method described in U.S. Pat. No. 6,316,002 ("the '002 patent). The entire content of the '002 patent is herein incorporated by reference. Through the unique spore-breaking method described in the '002 patent, the bioactive substances within the GASP are recovered in high yields and the functional activities of the bioactive substances are successfully preserved.

As shown below is a general description of the method used in the '002 patent, which leads to the production of the GASP:

I. Soaking to induce germination: Mature and perfect spores of *Ganoderma lucidum* were carefully selected to carry out a soaking process to induce germination. Spores were kept in clear or distilled water, biological saline solution, or other nutritional solutions that could enable the spores of *Ganoderma lucidum* to germinate rapidly. Examples of nutritional solutions include coconut juice or a 1-5% malt extract solution, 0.5-25% extracts of *Ganoderma lucidum* sporocarps or *Ganoderma lucidum* capillitia, 0.1-5% of culture solution containing biotin, 0.1-3% of culture solution containing monobasic potassium phosphate and magnesium sulfate. The choice of solution would depend on the soaking time required, the amount of spores to be processed and other such factors as availability of materials. One or more of the above germination solutions could be used, with the amount added being 0.1-5 times the weight of the spores of *Ganoderma lucidum*. The soaking time can be determined according to the temperature of the water, and usually the soaking was carried out for 30 min to 8 h with the temperature of the water at 20-43° C. Preferably soaking times were 2-4 hours, and temperature of the water was 25-35° C.

II. Activation culture: The spores of *Ganoderma lucidum* were removed from the soaking solution and excess water was eliminated by allowing it to drip. The spores were then placed in a well-ventilated culturing box at a constant temperature and humidity so that spore activation culture could be carried out. The relative humidity of the culture was generally set at 65-98%, the culture temperature at 18-48° C. and the activation time lasted from 30 min to 24 h. Preferably humidity is 85-97% and temperature is 25-35° C. Using the method provided by the present invention, the activation of spores of *Ganoderma lucidum* reached a rate of more than 95%. During activation, the cell walls of the spores of red *Ganoderma lucidum* were clearly softened such that it was easier to penetrate the cell walls of the spores.

III. Treatment of the epispores: After the germination activation process, the spores were treated by enzymolysis. This process was carried out at a low temperature and under conditions such that enzyme activity was maintained, using chitinase, cellulase, or other enzymes, which are commonly used in the industry. The process was complete when the epispores lost their resilience and became brittle. Alternatively, physical treatments were carried out to penetrate the cell walls, for example, micronization, roll pressing, grinding, super high pressure microstream treatment, and other mechanical methods commonly used in the industry could be carried out, with a penetration rate of over 99%.

IV. Drying or extraction: Drying was carried out at low temperature using standard methods including freeze-drying or vacuum-drying etc., which are commonly used in the industry. The obtained product had a moisture content less than 4%. After drying, the bioactive substances were extracted by water or alcohol, or by thin film condensation. The extracted bioactive substances could be further purified by dialysis to ensure no contamination in the final products.

V. Pharmaceutical formulations of the bioactive substances: The bioactive substances can then be made into purified powders, extract pastes, solutions for injection, or for oral consumption. The invention also encompasses the manufacture of pharmaceutical preparations of the active substances, using well-known expedients and methods of manufacture known in the art. In addition, the bioactive substances can be dosed by any convenient method including tablets, capsules, solutions, suppositories, nasal sprays, paranterals, or injection devices. The choice of method for administration is determined by the clinical situation of the patient. The bioactive substances of the present invention, produced by the methods described, include active genes, inducers of the biotic potential promotor, inducers of the multicellular activator, inducers of interferon, lactone A, *ganoderma* polysaccharide, *ganoderma* spore fatty acids, *ganoderma* spore long chain alkyl hydrocarbon, *ganoderma* triterpenes, sterols, superoxide dismutase, vitamin E, active glycoprotein, certain growth factors, *ganoderma* acid A, superoxide dismutases (SOD), active glycoproteins, multiple active enzymes, and growth factors and so on. These bioactive substances, in a whole, contribute to the therapeutic uses described in the later sections.

GASP are non-toxic. The preferred method for administering GASP is through oral uptake. Currently, GASP are approved by the Food and Drug Administration (FDA) to be used as dietary supplement in the capsule form under the name of Enhanvol® and Holistol, sold by Enhan Technology Holdings International Company, Ltd. in Hong Kong. Each capsule of GASP contains 0.3 g of GASP. The recommended dosage of GASP, when used as dietary supplement, is 4 times every day, 4 capsules each time. Thus, for an adult of 60 kg, the daily dosage of GASP as dietary supplement is at about 0.08 g/kg of body weight per day.

It has been shown, however, that no physiological and pathological abnormalities were found when 8 g/kg/day of GASP were given to patients and animals. 0.5 g to 15 g/kg/day of GASP have been given to animals and demonstrated significant effects on treatment of spinal cord injury. As shown in the following experimental designs, similar amount, i.e., 0.5 g to 15 g/kg/day of GASP, more favorably 1 g to 8 g/kg/day, given to animals has demonstrated significant effects on treatment of PD. It was further demonstrated that 1 g to 8 g/kg/day of GASP, more favorably about 5 g/kg/day, provided protective effects on dopaminergic neurons by improving the activities of tyrosine hydroxylase (TH) so as to convert DOPA to DA in the neurons. However, it is understood that the dosage for any particular patient depends upon a variety of factors, including age, body weight, general health, sex, diet, time of administration, route of administration, rate of excretion, drug combination and the severity of the disease. For these reasons, dosing is left to the discretion of the skilled clinician.

The following examples are illustrative, but not limiting the scope of the present invention. Reasonable variations, such as those occur to reasonable artisan, can be made herein without departing from the scope of the present invention.

Also in describing the invention, specific terminology is employed for the sake of clarity. However, the invention is not intended to be limited to the specific terminology so selected. It is to be understood that each specific element includes all technical equivalents which operate in a similar manner to accomplish a similar purpose.

Experiment 1

Behavioral Effects of GASP on Parkinson (PD) Animal Model

The pathogenesis of PD is chronic and progressive in nature, and it may take years and decades for PD to fully develop. It is also known that the magnitude of the toxin-induced brain lesion is dependent on the amount of 6-OHDA applied. In order to demonstrate the efficacy of the therapeutic agent in a very short time period (4 weeks) in a laboratory setting, very high doses of 6-OHDA (18 μg in 3 μL) and GASP (4 g per 100 g body weight) were selected. In comparison, it has been shown that 5 μg of 6-OHDA were sufficient to generate rat PD models, while a 2.5 μg of 6-OHDA was sufficient to generate an early PD model (Przedborski et al. *Neuroscience* 1995; 67(3):631-347). A dose of 4 g GASP per 100 g in rats is approximately equivalent to 300 g in a 60-kg human (i.e., the dose conversion among species is based upon the body surfaces).

I. Method

One hundred twenty (120) healthy male Sprague Dawley (SD) rats, weighing 210-240 grams, were purchased from Guangdong Province Medical Laboratory Animal Center and the Laboratory Animal Center of Sun Yat-sen University. The animals were randomized into three groups. The germination activated *Ganoderma lucidum* spore powders (GASP) were obtained from Enhan Technology Holdings International Company, Ltd., Hong Kong.

Preparation of PD models: The animals were anesthetized with an intraperitoneal injection of 10% chloral hydrate in the amount of 0.3-0.4 mL/100 g body weight. Following the "Stereotaxic Diagram of the Rat Brain" edited by Shin-Ming BAU, the anesthetized rat was immobilized in a stereotaxic frame. The hairs at the top of the head were shaved and locally disinfected. The skin was then cut open alone the mid-line from the front to the back of the rat skull. The soft tissues at the surface of the skull were separated to expose the perietal bone located at the right side of the head. The infusion site was set at the substantia nigra region of the right side of brain with the coordinates from Bregma as: AP −5.0 mm, ML +1.5 mm, and DV −8.8 mm. For animals receiving 6-OHDA, 6-OHDA (18 μg in 3 μL) was infused into the pre-selected site via a microinjector at the rate of 1 μL/min. After completion of 6-OHDA infusion, the needle was left at the infusion site for 10 minutes.

Treatment: The animals were treated as follows:
1) Group 1 (PD model control group) received a single 6-OHDA infusion only.
2) Group 2 (GASP treatment group) was given via gavage daily GASP at 4 g/100 g body weight for 3 consecutive days. The animals were then administered a single infusion of 6-OHDA.
3) Group 3 (normal control group) received a single injection of 0.2% ascorbic acid in normal saline at the same infusion site.

Evaluation of PD model: At one week after the 6-OHDA or ascorbic acid infusions all groups underwent behavioral assessment. The test animals received intraperitoneal injection of apomorphine 0.5 mg/kg and were observed for 30 minutes. If the rat constantly turned toward left with an average of more than 7 turns per minute, the rat was considered a successful PD model. If not, the rat was considered a unsuccessful PD model. The assessment was conducted once a week until the end of the fourth week.

II. Results

Among the 3 groups, no rats in the normal control group were observed to exhibit rotatary behavior. Of the 40 rats in the PD model control group, 25 rats had more than 6 rotation/minutes. In comparison, 10 rats in the GASP treatment group demonstrated rotatary behaviors.

The results of Pearson test comparing the PD model control group and the GASP treatment group indicated that there was statistically significant difference between the two groups (p=0.001, p<0.01). This indicated that GASP provided brain protection against 6-OHDA induced PD development.

III. Conclusion

The data suggested that GASP may prevent the occurrence of PD.

Experiment 2

Microstructures in PD Animal Model and the Treatment Effects of GASP

I. Method

At the end of the fourth week, six (6) rats per group were selected from the animals in Experiment 1, the rats were anesthetized using an intraperitoneal injection of 10% choral hydrate at 0.5 mL/100 g body weight. The thoracic cavity was opened and the brain tissue was promptly fixated via rapid perfusion of an electronic microscope solution. The cranial cavity was then dissected opened and the brain tissue was removed. The ventral section of the right side of midbrain (mesencephalon) was separated. Samples of substantia nigra were then prepared and observed under electronic microscope.

II. Results

Figure 1:
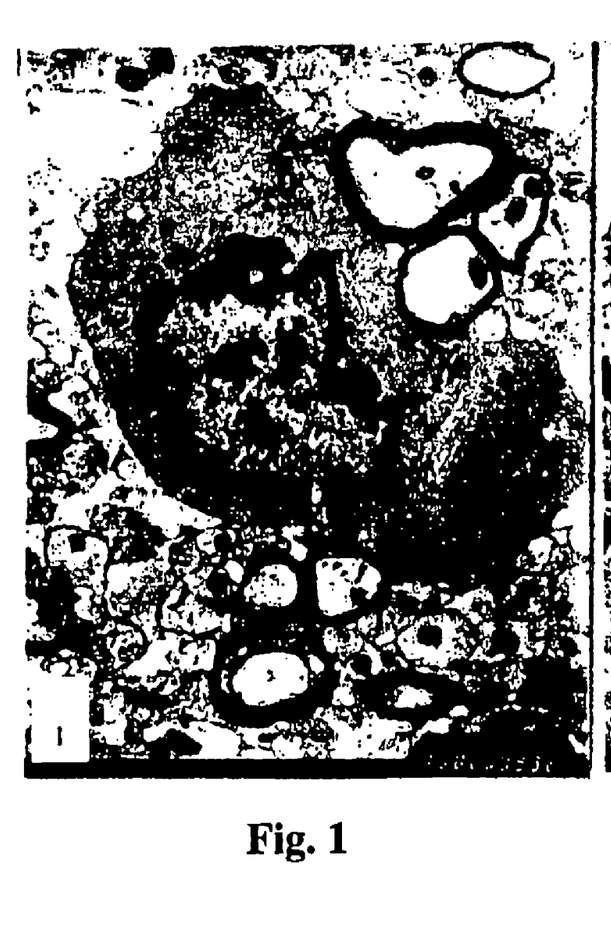
FIGS. 1 and 2 show the substantia nigra region of the brain of the rat in the PD model control group, which demonstrates chromatin condensation and margination, typical phenomena of cell apoptosis. In addition, unclear outline of mitochondria, dilation of endoplasmic reticulum, and swelling of nerve fiber were also observed.
Figure 2:
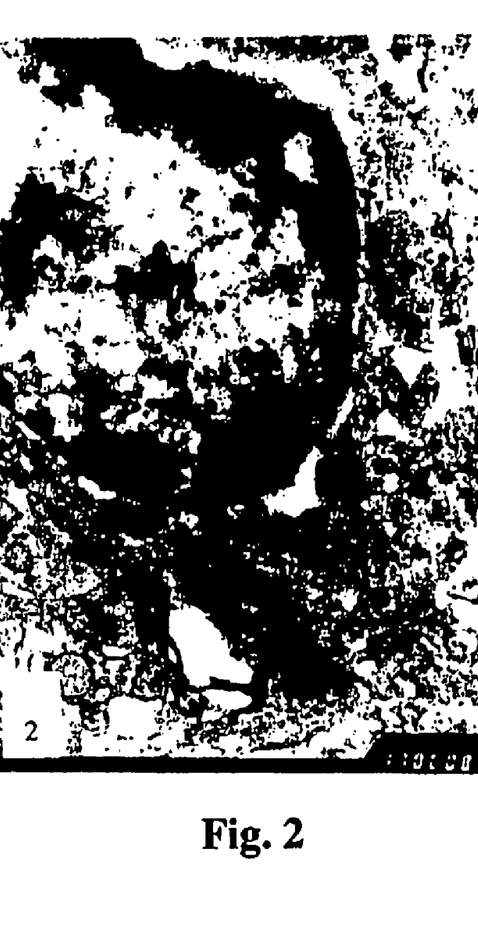

Group 1 (PD model control group): In the nigral samples from six successful PD models, more nerve cells showed chromatin condensation and margination that were typical phenomena of cell apoptosis. In addition, unclear outline of mitochondria, dilation of endoplasmic reticulum, swelling of nerve fiber were also observed. Furthermore, chromatin condensation and margination were also observed in the glia cells. See FIGS. 1 and 2.

Figure 3:
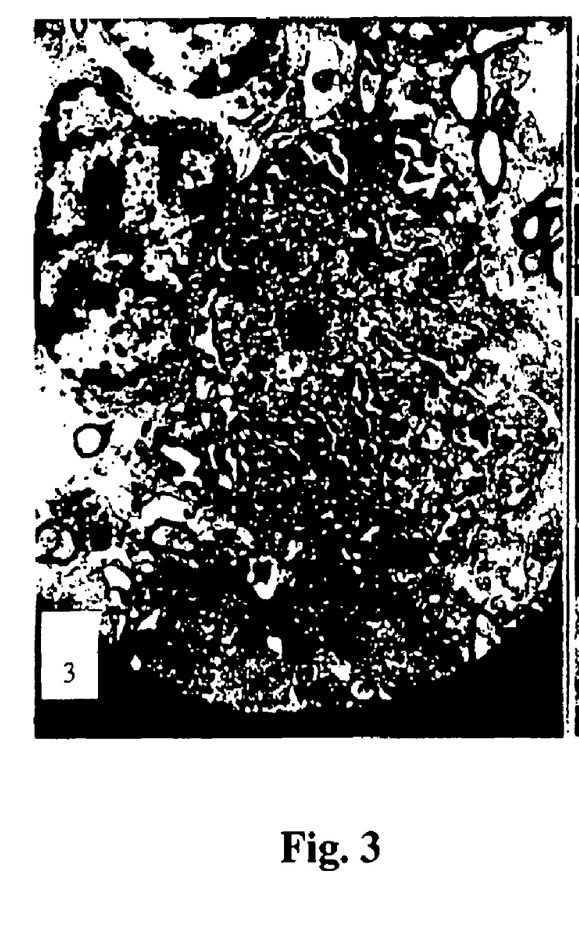
FIGS. 3 and 4 show the substantia nigra region of the brain of the rat in the GASP treatment group. Infrequent apoptosis of neurons was observed. Some unclear outline of mitochondria and dilation of endoplasmic reticulum were observed.
Figure 4:
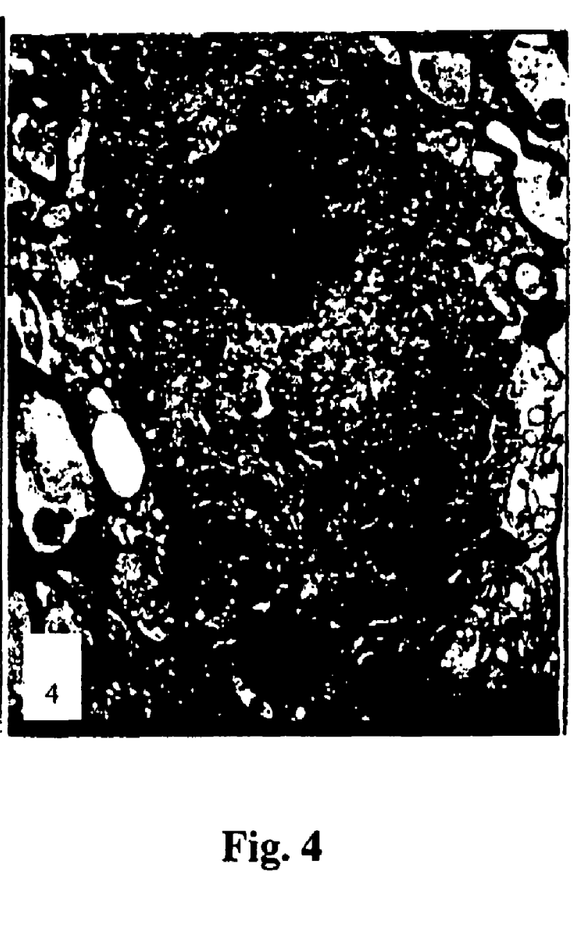

Group 2 (GASP treatment group): Substantia nigra samples were prepared from the six rats having the most turns. Infrequent apoptosis of neurons was observed. Some unclear outline of mitochondria and dilation of endoplasmic reticulum were observed. See FIGS. 3 and 4.

Figure 5:
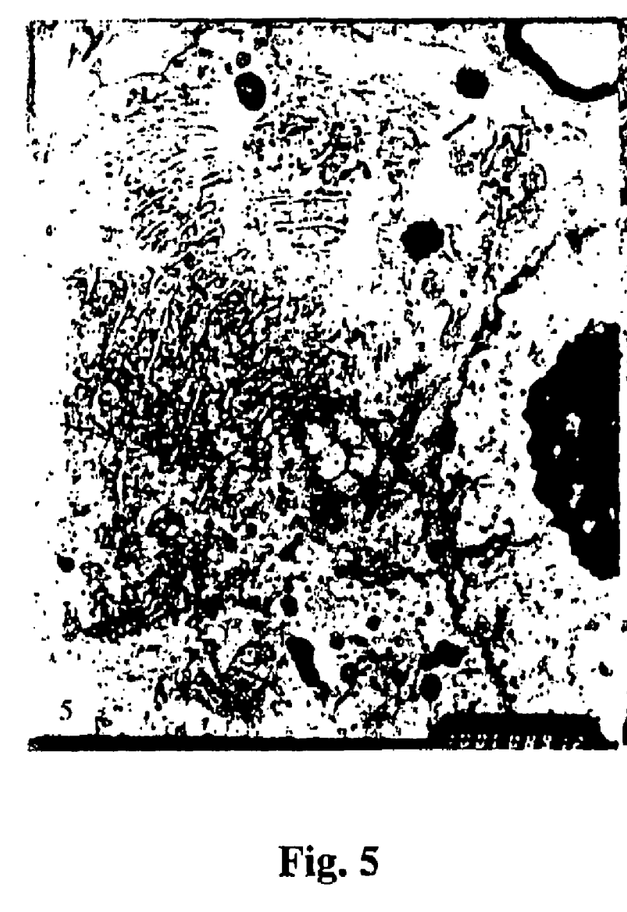
FIGS. 5 and 6 show the substantia nigra region of the brain of normal control rats. Clear nuclei and cell organelles were found in normal neurons.
Figure 6:
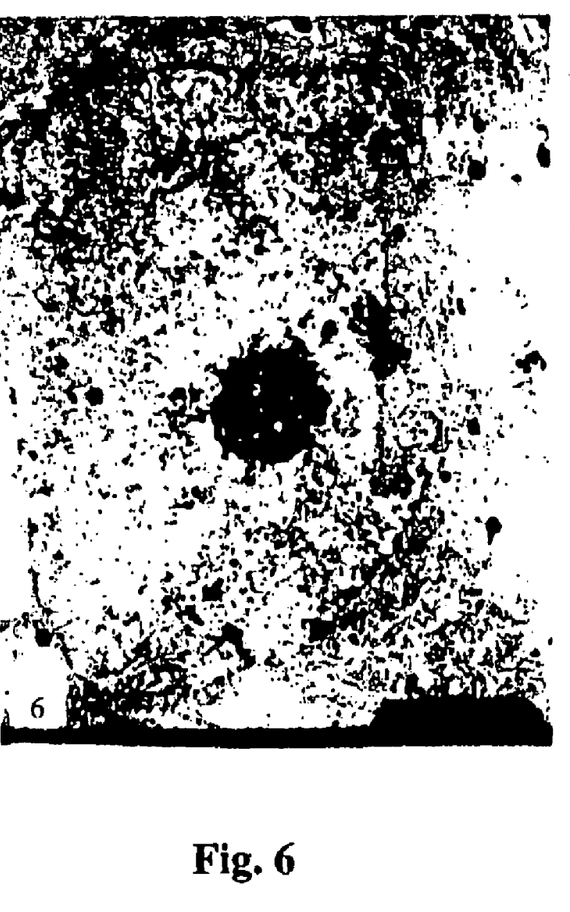

Group 3 (normal control group): There was no remarkable changes in neurons or nerve fibers in the brain samples. See FIGS. 5 and 6.

III. Conclusion

Based upon the morphologic findings, GASP may have inhibitory activity on neuron apoptosis and be able to provide protection for the brain.

Experiment 3. Effects of GASP on Tyrosine Hydroxylase (TH)

Dopamine is synthesized from tyrosine in the neurons in the substantia nigra. The rate-limiting step in this enzymatic process is the conversion of tyrosine to dihydroxyphenylalanine (levodopa) catalyzed by tyrosine hydroxylase (TH). Levodopa is then enzymatically decarboxylated to form dopamine. Thus, the presence of TH can be used to indicate the presence of the dopamine-producing neurons.

Part 1. Qualitative Study of the Effects of GASP on Tyrosine Hydroxylase (TH)

I. Method

Randomization of rats, PD model preparation and GASP treatments were carried out according to Experiment 1, supra. Rats that fulfilled the criteria were selected, sacrificed, and fixated by perfusion. The substantia nigra and striatum were separated, fixed in paraffin and then sliced. TH on the paraffin slices were detected using immunologic assay. The procedures are described in more details in the following sections.

Fixation of brain tissue: The rats were deep anesthetized using 10% choral hydrate. The limbs of rats were straightened and secured on a board with the ventral side up. The skin surface of the xiphoid process was cut open for separation of the xiphoid process. Using a forcep to hold the xiphoid process, the costal cartilage at both sides of sternum were cut through to expose heart in the thoracic cavity and liver in the peritoneal cavity. The beating heart was gently held using a long forcep for opening a small hole at the apex. A perfusion needle was inserted through the opening into the left ventricle and into the aorta. The long forcep was clamped to securely hold the heart and the perfusion needle. The inferior vena cava was cut open and the mixture of heparin (100μ/2 ampoules) and physiological saline (500 mL) was rapidly perfused into the rat, until the effluent at the inferior vena cava turned light red. The rapid perfusion was continued with 4% paraformaldehyde perfusion solution. Slight tremors of head and limbs and stiff body indicated a good perfusion result. Perfusion was discontinued at 10 minutes later and about 170 mL of 4% paraformaldehyde solution had been used. Whole brain was then removed to harvest the midbrain and the striatum at both sides. They were dissected into 1×1×0.5 $cm^3$ cubes and fixed in 4% paraformaldehyde for 4-6 hours.

Dehydration and embedding of the brain tissue: The fixed cubes of brain tissues were dehydrated in an automatic dehydrator, Leica TP 1010 (German) for 16-17 hours and then embedded in paraffin in a paraffin embedding machine, Leica EG 1160 (German) as follows. At room temperature, 1) dehydration: 70% ethanol for 12-20 hours, then 80% ethanol for 2-4 hours, then 95% ethanol for 2-4 hours, then 100% ethanol for 1-2 hours, then xylene for 15 minutes, then paraffin (60° C.) for 1-2 hours; 2) soaking: in paraffin (60° C.) 1-3 hours; 3) embedding: embedded in 62° C. embedding wax; 4) slicing: placing the resultant slices of 4-5 μm thickness at 37° C. for 2 hours, then placed in 4° C. refrigerator for long term storage.

Immunohistochemistry of brain tissue TH: The brain tissue specimens were stained using the LSAB method (streptavidin-biotin immunoperoxidase method). The procedure was as follows:

1) The embedded rat brain tissues were sliced into 5 μm slices using a rotary microtome (Leica RM 2135, German).

The slices were baked under 60° C. for 2 hours, then placed in xylene to deparaffinize for 10 minutes twice, then placed in gradient ethanol solutions (100%, 95%, 80%, 70%) for 5 minutes each, then washed with distilled water for 5 minutes twice.

2) The slices were placed in freshly prepared 3% $H_2O_2$ solution to quench the activity of endogenous peroxidase at room temperature for 5 minutes then washed with 3 changes of distilled water for 5 minutes each.

3) Epitope retrieval: The slices were placed in 0.01M trisodium citrate solution (pH 6.0) for microwave eptiope retrieval for 10 minutes. After cooling to the room temperature, the slices were removed and washed with 2 changes of 0.1M PBS for 3 minutes each.

4) Normal goat serum blocking solution was added dropwise and left at room temperature for 10 minutes. The excessive solution was removed without washing.

5) After blotting away the excessive goat serum solution with filter paper and adding the primary antibody (1:8000), the slides were placed in 4° C. refrigerator overnight then washed with 3 changes of 0.1M PBS for 5 minutes each.

6) After addition of biotinylated secondary antibody at 37° C. for 20 minutes, the slides were washed with 3 changes of PBS for 5 minutes each.

7) The peroxidase label (streptavidin complex) were applied and the slides were incubated at 37° C. for 20 minutes then washed with 3 changes of 0.1M PBS for 5 minutes each.

8) The slides were stained with freshly prepared DAB and developed under microscope for an appropriate time, then rinsed with tap water. The nuclei were counter-stained with hematoxylin. The tissues were dehydrated through an ethanol gradient and xylene and sealed in neutral gum.

Analysis and Comparison of the Immunohistochemistry Results of Brain Tissue TH

Cells with polygonal shape and appearance of brown color in cytoplasma were identified as TH positive cells.

The number of TH positive cells in the midbrain substantia nigra were counted under microscope using imagine analyzer. Three vision fields (each with an area of 43157.37 $\mu m^3$) were observed under 10×20 magnification for each side of brain. The average number of TH positive cells from the three vision fields represented the number of TH positive cells of this side of brain.

The numbers of TH positive cells and fibrous cells in the substantia nigra and striatum of both sides of brain were counted for each of animals from the normal control, PD model control and GASP treatment groups. Comparisons were made between two groups and the results were indicated as "decrease" or "increase".

Part 2. Semi-Quantitative Study of the Effects of GASP on TH

I. Method

The expression of TH was determined using Western Blot.

II. Procedures

1) Extraction of total protein in midbrain: Ten animals from each of the groups were selected and sacrificed to remove the ventral section (70 mg) of the right midbrain. The tissue was placed in frozen storage tube and stored under liquid nitrogen.

2) The frozen tissue was retrieved from the liquid nitrogen, washed with 0.1M PBS, placed in 500 μL of decontamination disintegrating solution [50 mM Tris-HCl pH 8.0, 0.1% SDS, 150 mM NaCl, 0.02% sodium azide, 100 μg/mL PMSF (phenylmethyl sulfonyl fluoride), protease inhibitor complex 1% Nonidet P-40 (NP-40), 0.5% sodium desoxycholate], homogenized, and centrifuged at 1500 rpm. The supernatants were collected and stored in −20° C. refrigerator.

3) 80 μL of the protein sample was mixed in 20 μL of the buffer above and boiled for 5 minutes, then awaited testing.

4) Preparation of polyacrylamide gel: First, the 10% running gel was prepared as mixing double distilled water 3.2 mL, 30% polyacrylamide 2.64 mL, 1.5M Tris (pH 8.8) 2 mL, 10% SDS 0.08 mL, 10% ammonium persulfate 0.08 mL, and TEMED 0.006 mL and placed in the chamber. The 5% stacking gel was prepared by mixing double distilled water 2.2 mL, 30% polyacrylamide 0.67 mL, 1M Tris (pH 6.8) 1 mL, 10% SDS 0.04 mL, 10% ammonium persulfate 0.04 mL, and TEMED 0.004 mL, and then placed in the chamber.

5) SDS-polyacrylamide gel electrophoresis (PAGE): 25 μL of the supernatant sample was isolated by electrophoresis under constant 80V for 20 minutes then adjusted to 120 V for 100 minutes until the bromo phenol blue indicator had moved out of the bottom of the running gel.

6) Transfer: The gel was then soaked in transfer buffer (25 mM trisbase, 0.2M glycine, 20% methanol, pH 8.5) for 5 minutes, and moved to the transferring rack near the side of the negative electrode. Nitrocellulose member (manufactured by Pall) which was pre-soaked in the transfer buffer for 30 minutes was tightly placed on top of the gel. Air bubbles were removed. Member transfer was conducted at 4° C. under a constant current of 0.3 A for 100 minutes.

7) Antibody labeling: The nitrocellulose membrane was retrieved and placed in 1× TBS (20 mM Trisbase, 137 mM NaCl) with shaking for 15 minutes to remove the transfer buffer. The membrane was then blocked in 5 mL of 3% BSA TBS blocking solution at room temperature for 2 hours. The membrane was then washed with 3 changes of 0.1% TBS/T for 10 minutes each. The nitrocellulose membrane was incubated overnight in 6 mL of TH multiclonal antibody (diluted by 1:2000) at 4° C. with shaking. On next day, the membrane was washed with 3 changes of 15 mL 0.1% TBS/T for 10 minutes each. The membrane was then incubated in the mixture of secondary antibody (1:2000) and HRP-anti-biotin antibody (1:1000) in 10 mL blocking solution at room temperature for 1 hour.

8) Exposure: The membrane was washed with 3 changes of 15 mL 0.1% TBS/T for 10 minutes each, then placed in 2.2 mL LumiGlo (containing 0.1 mL 20× LumiGLO™, 0.1 mL 20× $H_2O_2$ in 2 mL double distilled water) at room temperature with shaking for 1 minute. The membrane was exposed to x-ray in a dark room for several seconds to minutes, developed for 1 minute, fixed for 4 minutes, rinsed and then dried. The membrane was then photographed and underwent imagine analysis.

Part 3. Effects of GASP Treatment on the Expression of TH mRNA

I. Method

In situ hybridization using the following probes (DIG-Labeled Probe Detection kit obtained from Wuhen BoSeDe Company) were carried out:

(1) rat:    5'-GTTTG AGACA TTTGA AGCCA AAATC CACCA-3'  (SEQ ID NO: 1)

(2) mouse:  5'-CTGGT TCCCA AGGAA AGTGT CAGAG TTGGA-3'  (SEQ ID NO: 2)

(3) human:  5'-TTCTC TGTGA AGTTT GACCC GTACA CCCTG-3'  (SEQ ID NO: 3)

II. Procedures

1) Ten rats were selected from each of the three groups and sacrificed. The midbrain was collected and placed in 30% sucrose solution overnight and precipitated.

2) The brain tissue was frozen-sectioned.

3) The slices were fixed in 4% parpformaldehyde/0.1M PBS (1/1000 DEPC) at room temperature for 20-30 minutes and then thoroughly washed with distilled water. After drying, the slices were packed in aluminum foil and stored at −20° C.

4) The slices were processed in freshly prepared 0.5% $H_2O_2$/methanol solution at room temperature for 30 minutes and then washed with 3 changes of double distilled water for 5 minutes each.

5) The slices were digested in freshly diluted 3% citric acid solution of gastric pro0tease at room temperature for 10 seconds then washed with 3 changes of 0.5M PBS for 5 minutes each and then washed with double distilled water.

6) Pre-hybridization: 20% glycerin was first placed at the bottom of each hybridization dish to maintain the moisture content. 40 μL of the pre-hybridization solution was added to the slice in each culture dish, incubated at a 37° C. incubator for 3 hours. 0Excessive liquid was removed without washing.

7) Hybridization: 40 μL of hybridization solution was added to each cultural dish. The dish cover was put in place. The dishes were incubated at a 37° C. incubator overnight.

8) After hybridization: After removing the dish cover, the slice was washed with 2 changes of 2×SSC (30-37° C.) for 5 minutes each; one wash of 15 mL 0.5×SSC for 15 minutes; then one wash of 0.2×SSC for 15 minutes.

9) A blocking solution was added dropwise to the slice and incubated at 37° C. for 30 minutes. Excessive liquid was removed without washing.

10) A solution of the rat biotinylated anti-DIG antibody was added dropwise and incubated at 37° C. for 60 minutes, then washed with 4 changes of 0.5M PBS for 5 minutes each.

11) A solution of SABC was added dropwise and incubated at 37° C. for 20 minutes, then washed with 3 changes of 0.5M PBS for 5 minutes each.

12) A solution of biotinylated peroxidase was added dropwise and incubated at 37° C. for 20 minutes, then washed with 4 changes of 0.5M PBS for 5 minutes each.

13) A solution of diluted DAB developer was added dropwise, the slices were developed for 20-30 minutes and then thoroughly rinsed. After drying, the slices were sealed using a water-soluble sealant.

Results

Part 1. Qualitative Study of the Effects of GASP on Tyrosine Hydroxylase (TH)

Figure 7:
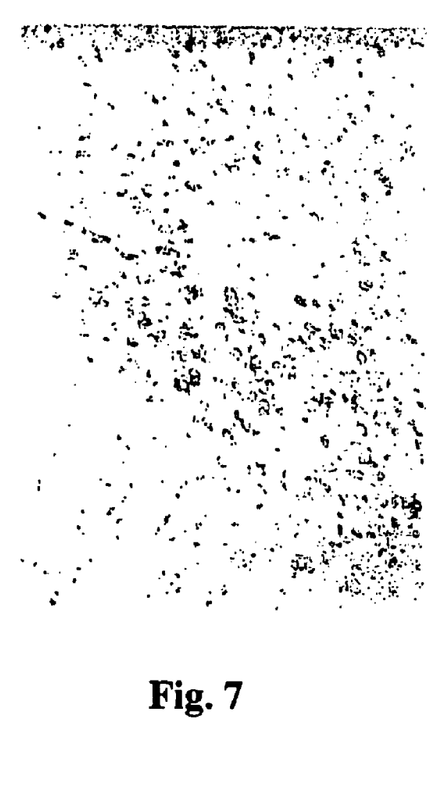
FIGS. 7, 8 and 9 show the immunohistochemistry of tyrosine hydroxylase (TH) in animals of the normal control (FIG. 7), the PD model control (FIG. 8) and the GASP treatment (FIG. 9) groups, respectively. There is a marked reduction in the numbers of TH positive cells in the PD model control group when comparing to the normal control group (FIG. 8 vs.
Figure 8:
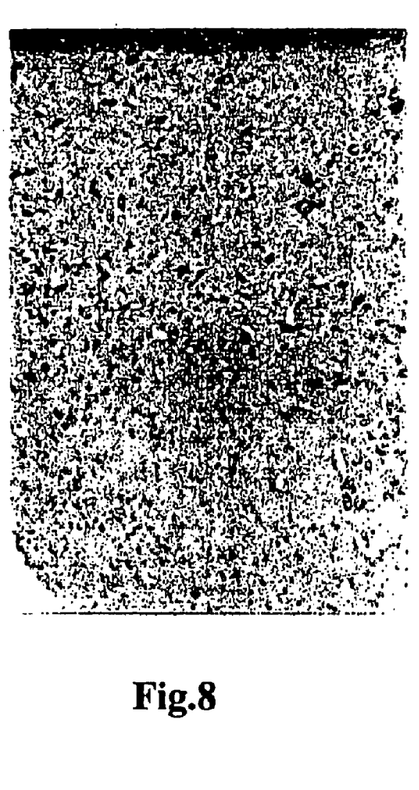
Figure 9:
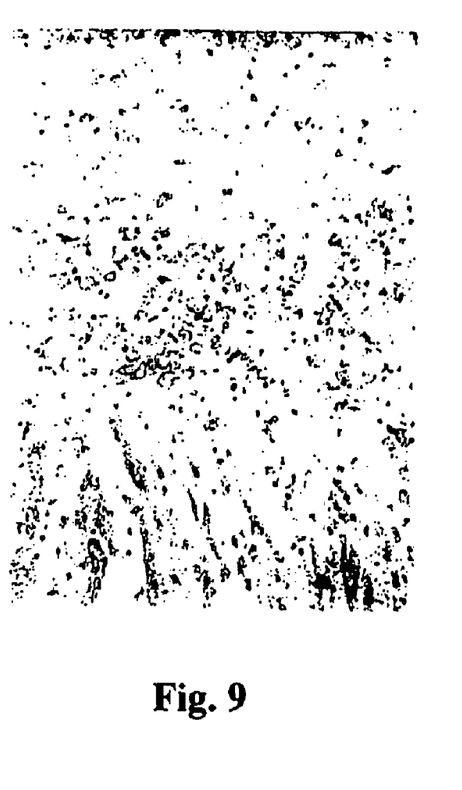

As shown in FIGS. 7, 8, and 9, the PD model control group had markedly reduced numbers of TH positive neurons than the normal control group. The GASP treatment group had markedly increased numbers of TH positive neurons than the PD model control group.

Part 2. Semi-Quantitative Study of the Effects of GASP on TH

Figure 13:
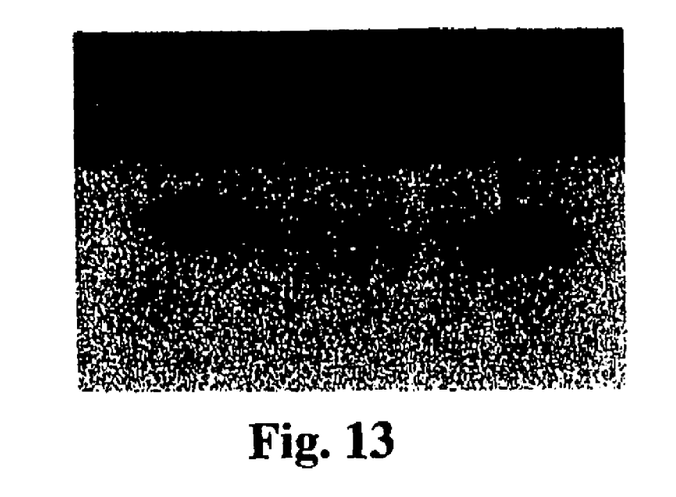
FIG. 13 shows the Western Blot results of TH protein expression in the animals of the normal control (left lane), the PD model control (middle lane) and the GASP treatment (right lane) groups. TH protein expressions in the GASP treatment group and the normal control groups were higher than that of the PD model control group.

Protein expression of TH in the PD model control was markedly less than that of the normal control group. The protein expression in the GASP treatment group was markedly more than that of the PD model control group. See FIG. 13.

Part 3. Effects of GASP Treatment on the Expression of TH mRNA

Figure 15:
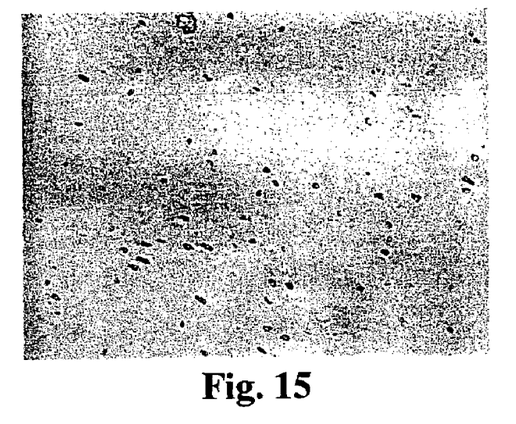
FIGS. 15, 16, and 17 show the in situ hybridization results of TH mRNA in the animals of the normal control (FIG. 15), the PD model control (FIG. 16) and the GASP treatment (FIG. 17) groups, respectively. TH mRNA expressions in the GASP treatment group and the normal control groups were higher than that of the PD model control group.
Figure 16:
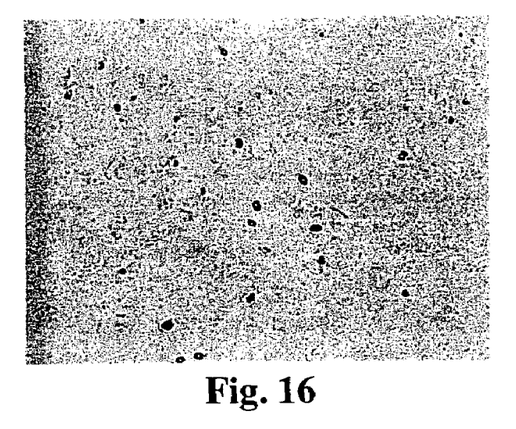
Figure 17:
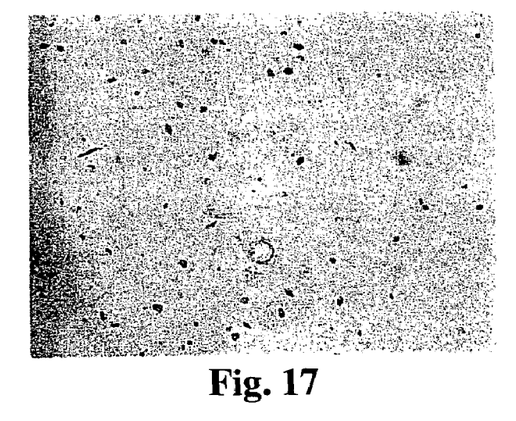

Hybridization of TH mRNA in the PD model control was markedly less than that of the normal control group. The hybridization of TH mRNA in the GASP treatment group was markedly more than that of the PD model control group. See FIGS. 15, 16 and 17.

Conclusion

Current findings of PD model animals having less numbers of TH positive neurons and DA production (see also Experiment 5, infra) than those of normal animals agreed with the literature. Treatment with GASP enhanced the numbers of TH positive neurons and DA production and increased the levels of TH and DA in the brain tissues, indicating that GASP have protective effects on the TH-positive neurons.

Experiment 4

Effects of GASP Treatment on the Apoptosis Protease (Caspase 3) in the Midbrain of the PD Models Part 1. Qualitative Study of the Effects of GASP on the Midbrain Apoptosis Protease (Caspase 3) of the PD Model The study was carried out using the immunohistochemistry method as described in Experiment 3, Part 1, supra.

Part 2. Semi-Quantitative Study of the Effects of GASP on the Midbrain Apoptosis Protease (Caspase 3) of the PD Model The study was carried out using the Western Blot method as described in Experiment 3, Part 2, supra.

Part 3. Effects of GASP Treatment on mRNA Expression of the Midbrain Apoptosis Protease (Caspase 3) of the PD Model The study was carried out using the in situ hybridization method as described in Experiment 3, Part 3, supra, and using the following caspase 3 hybridization probes:

(1) Rat:    5'-CTGGACAACAGTTATAAAATGGATTATCCT-3'  (SEQ ID NO: 4)

(2) Mouse:  5'-TATTCAGGCCTGCCGTGGATCAGAACTGGA-3'  (SEQ ID NO: 5)

(3) Human:  5'-TAACCGAAAGGTGGCAACAGAATTTGAGTC-3'  (SEQ ID NO: 6)

Results

Figure 10:
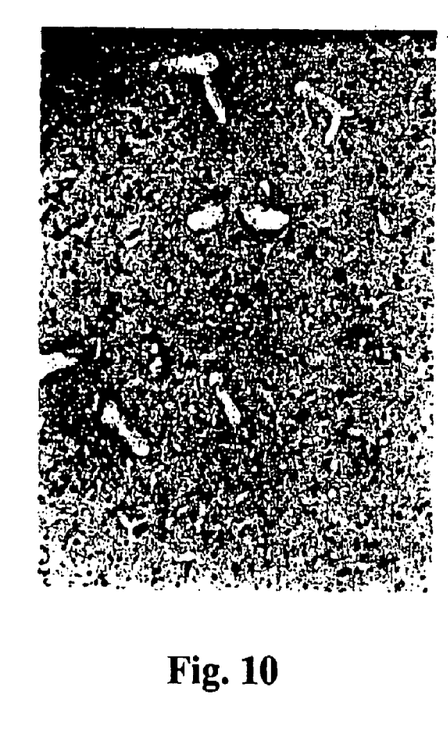
FIGS. 10, 11, and 12 show the immunohistochemistry of caspase 3 in animals of the normal control (FIG. 7), the PD model control (FIG. 8) and the GASP treatment groups (FIG. 9), respectively. There is a marked increase in the numbers of caspase 3 positive cells in the PD model control group when comparing to the normal control group (FIG. 11 vs.
Figure 11:
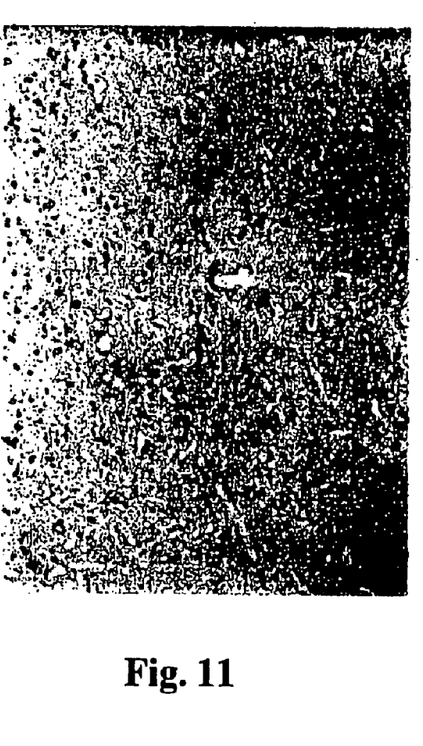
Figure 12:
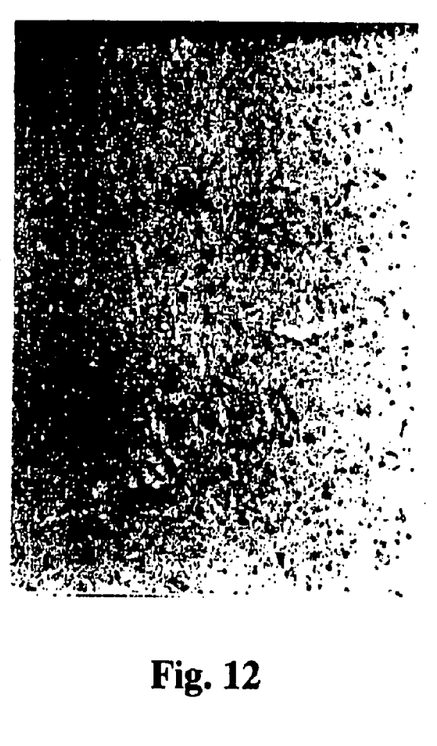

Part 1. Qualitative Study of the Eeffects of GASP on the Midbrain Apoptosis Protease (Caspase 3) of the PD Model As shown in FIGS. 10, 11, and 12, the PD model control group had markedly more numbers of caspase 3 positive neurons than the normal control group. The GASP treatment group had markedly reduced numbers of caspase 3 positive neurons than the PD model control group.

Figure 14:
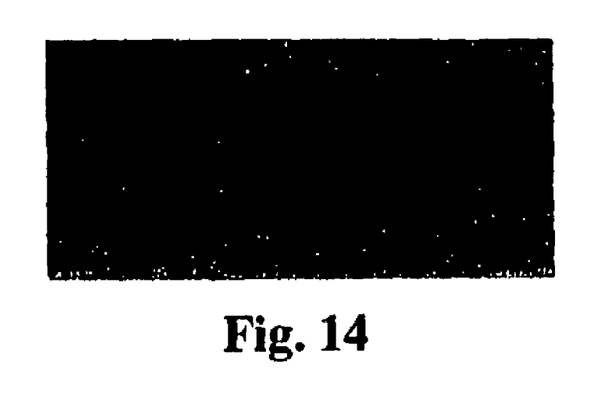
FIG. 14 shows the Western Blot results of caspase 3 protein expression in the animals of the normal control (left lane), the PD model control (middle lane) and the GASP treatment (right lane) groups. Caspase 3 protein expression was highest in the PD model control group.

Part 2. Semi-Quantitative Study of the Effects of GASP on the Midbrain Apoptosis Protease (Caspase 3) of the PD Model Protein expression of caspase 3 in the PD model control group was markedly higher than that of the normal control group. Protein expression of caspase 3 of the GASP treatment group was markedly lower than that of the PD model control group. See FIG. 14.

Figure 18:
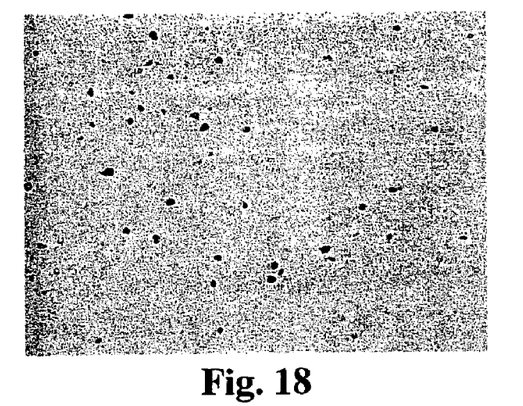
FIGS. 18, 19 and 20 show the in situ hybridization results of caspase 3 mRNA in the animals of the normal control (FIG. 18), the PD model control (FIG. 19) and the GASP treatment (FIG. 20) groups, respectively. Caspase 3 mRNA expression was highest in the PD model control group.
Figure 19:
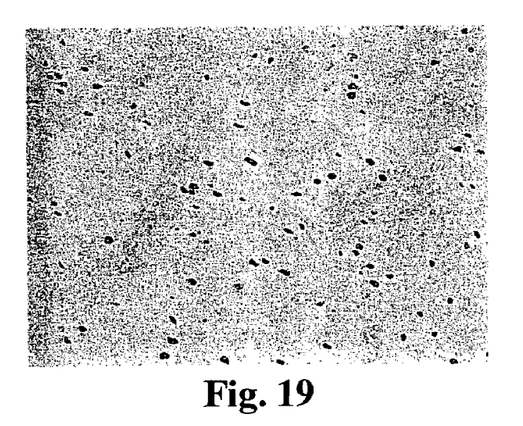
Figure 20:
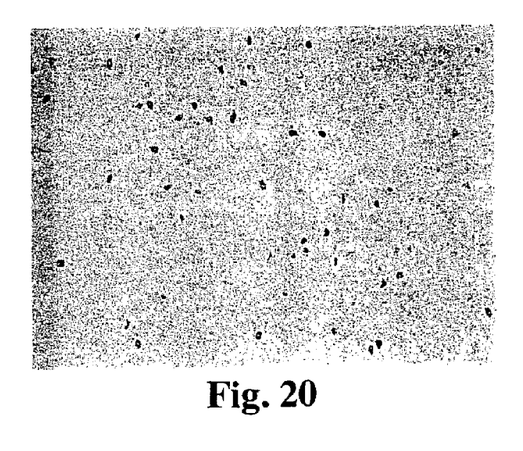

Part 3. Effects of GASP Treatment on mRNA Expression of the Midbrain Apoptosis Protease (Caspase 3) of the PD Model Numbers of cells with positive hybridization of caspase 3 mRNA in the PD model control were markedly higher than those of the normal control group. Numbers of cells with positive hybridization of caspase 3 mRNA in the GASP treatment group were markedly less than those of the PD model control group. See FIGS. 18, 19, and 20.

Conclusion

GASP have protective effects against neuron apoptosis. The results of caspase 3 study and electronic microscope observation (Experiment 2) indicate that apoptosis may play a important role in the pathogenesis of PD that cell apoptosis is an important step in the death of the substantia nigra dopaminergic neurons.

Experiment 5

Effects of GASP on Dopamine (DA) of the Substantia Nigra

The amount of dopamine and metabolites in the substantia nigra was determined using HPLC.

Thirty (30) male rats were separated into 3 groups: normal control group, PD model control group and GASP treatment group. The PD model preparation for animals in the PD model control and GASP treatment groups were performed following the procedures as previously described in Experiment 1. After two weeks, the animals were sacrificed and the midbrains were collected and placed in liquid nitrogen. The brain tissue was retrieved from the liquid nitrogen and homogenized in 1 mL previously chilled perchloric acid. The mixture was centrifuged at 4° C. at 15000 rpm for 30 minutes. The supernatants were collected.

The supernatant samples (20 μL) and standard solutions were analyzed by HPLC under the following conditions:

1) A buffer of 3 mM sodium heptanesulfate, 100 mM sodium acetate, 85 mM citric acid, 0.2M EDTA, pH adjusted to 3.7 was used. The mobile phase was the 92:8 mixture of the above buffer and methanol. The detector was equipped with glass carbon electrodes. The detector voltage was 0.6V, and the high pressure pump provided a flow rate of 0.8 mL/minute.

2) Qualitative analysis: by comparing the retention time of the sample peak to that of the standard.

3) Quantitative analysis: DHBA was used as the internal standard, the peak area of the sample peak was compared to that of the DHBA peak to determine the amount of the sample.

Results

The results of the DA analysis for each group are presented in Table 1. As seen in Table 1, The GASP treatment group had statistically significantly higher contents of substantia nigra DA and metabolites than those of the PD model control group ($p<0.001$).

TABLE 1

| DA contents in the substantia nigra at the surgical side after PD model preparation and treatment | |
|---|---|
| Group | DA content (ng/g wet wt. of the substantia nigra) |
| Normal control | 574.4597 ± 328.3309* |
| PD model control | 356.9653 ± 195.9975 |
| GASP treatment | 829.1706 ± 544.0212* |

Note:
the comparison was made to the PD model control group.
*$p < 0.001$.

Conclusion

GASP treatment increased the production of DA in PD rats. This finding together with the result that GASP treatment increased the TH positive neurons in PD rats (see also Example 3) indicated that GASP provided protection for the dopaminergic neurons in the substantia nigra.

While the invention has been described by way of examples and in term of the preferred embodiments, it is to be understood that the invention is not limited to the disclosed embodiments. On the contrary, it is intended to cover various modifications as would be apparent to those skilled in the art. Therefore, the scope of the appended claims should be accorded the broadest interpretation so as to encompass all such modifications.

We claim:

1. A method for treating Parkinson's disease comprising administering to a mammal in need thereof an effective amount of sporoderm-broken germination activated *Ganoderma lucidum* spores (GASP);

wherein said sporoderm-broken GASP are produced by soaking *Ganoderma lucidum* spores in a solution which is selected from the group consisting of water, saline, and a nutritional solution to cause to produce germinated *Ganoderma lucidum* spores;

placing said germinated *Ganoderma lucidum* spores in a culture box to activate said germinated spores at relative humidity of 65-98% and temperature of 18-48° C. to produce germination-activated *Ganoderma lucidum* spores so as to enhance production of bioactive substances in said germination activated *Ganoderma luidum* spores; and treating said germination activated *Ganoderma luidum* spores with an enzyme with cell wall dissolving property and/or a mechanical means to produce said sporoderm-broken GASP.

2. The method according to claim 1, wherein said mammal is a human.

3. The method according to claim 1, wherein said Parkinson's disease is at an early stage.

4. The method according to claim 1, wherein said effective amount is about 0.5 to 15 g per kg per day.

5. The method according to claim 1, wherein said effective amount is about 1 and 8 g per kg per day.

6. The method according to claim 1, wherein said sporoderm-broken GASP is orally administered to said mammal.

7. The method according to claim 1, wherein said sporoderm-broken GASP reduces symptom of rotatary behavior.

8. The method according to claim 1, wherein said sporoderm-broken GASP reduces progression of neuron apoptosis in substantia nigra.

9. The method according to claim 1, wherein said sporoderm-broken GASP improves tyrosine hydroxylase activity in neurons.

10. The method according to claim 9, wherein said sporoderm-broken GASP improves dopamine production in neurons.

11. A method for protecting dopaminergic neurons from neuron apoptosis in a mammal comprising in need thereof administering to said mammal an effective amount of germination activated sporoderm-broken germination activated *Ganoderma luidum* spores (GASP);
   wherein said sporoderm-broken GASP are produced by soaking *Ganoderma lucidum* spores in a solution which is selected from the group consisting of water, saline, and a nutritional solution to cause to produce germinated *Ganoderma luidum* spores;
   placing said germinated *Ganoderma luidum* spores in a culture box to activate said germinated spores at relative humidity of 65-98% and temperature of 18-48° C. to produce germination-activated *Ganoderma luidum* spores so as to enhance production of bioactive substances in said germination activated *Ganoderma luidum* spores; and
   treating said germination activated *Ganoderma luidum* spores with an enzyme with cell wall dissolving property and/or a mechanical means to produce said sporoderm-broken GASP.

12. The method according to claim 11, wherein said mammal is a human.

13. The method according to claim 11, wherein said sporoderm-broken GASP is orally administered to said mammal.

14. The method according to claim 11, wherein said sporoderm-broken GASP increases tyrosine hydroxylase activity in said dopaminergic neurons.

15. The method according to claim 14, wherein said sporoderm-broken GASP increases dopamine production in said dopaminergic neurons.

16. A method for increasing tyrosine hydroxylase activity in dopaminergic neurons of a mammal comprising in need thereof administering to said mammal an effective amount of sporoderm-broken germination activated *Ganoderma lucidum* spores (GASP);
   wherein said sporoderm-broken GASP are produced by soaking *Ganoderma lucidum* spores in a solution which is selected from the group consisting of water, saline, and a nutritional solution to cause to produce germinated *Ganoderma luidum* spores;
   placing said germinated *Ganoderma luidum* spores in a culture box to activate said germinated spores at relative humidity of 65-98% and temperature of 18-48° C. to produce germination-activated *Ganoderma luidum* spores so as to enhance production of bioactive substances in said germination activated *Ganoderma luidum* spores and
   treating said germination activated *Ganoderma luidum* spores with an enzyme with cell wall dissolving property and/or a mechanical means to produce said sporoderm-broken GASP.

17. The method according to claim 16, wherein said mammal is a human.

18. The method according to claim 16, wherein said sporoderm-broken GASP is orally administered to said mammal.

19. The method according to claim 16, wherein said sporoderm-broken GASP increases conversion of hydroxydopamine to dopamine.

20. The method according to claim 1, wherein said enzyme with cell wall dissolving property is chihinase or cellulose.

21. The method according to claim 1, wherein said mechanical means is micronization, roll pressing, grinding, or super high pressure microstream.

* * * * *

SEQUENCE LISTING

<160> NUMBER OF SEQ ID NOS: 6

<210> SEQ ID NO 1
<211> LENGTH: 30
<212> TYPE: DNA
<213> ORGANISM: artificial sequence
<220> FEATURE:
<223> OTHER INFORMATION: probe for rat tyrosine hydroxylase mRNA

<400> SEQUENCE: 1
gtttgagaca tttgaagcca aaatccacca                                    30

<210> SEQ ID NO 2

```
<211> LENGTH: 30
<212> TYPE: DNA
<213> ORGANISM: artificial sequence
<220> FEATURE:
<223> OTHER INFORMATION: probe for mouse tyrosine hydroxylase mRNA

<400> SEQUENCE: 2
ctggttccca aggaaagtgt cagagttgga                                30

<210> SEQ ID NO 3
<211> LENGTH: 30
<212> TYPE: DNA
<213> ORGANISM: artificial sequence
<220> FEATURE:
<223> OTHER INFORMATION: probe for human tyrosine hydroxylase mRNA

<400> SEQUENCE: 3
ttctctgtga agtttgaccc gtacaccctg                                30

<210> SEQ ID NO 4
<211> LENGTH: 30
<212> TYPE: DNA
<213> ORGANISM: artificial sequence
<220> FEATURE:
<223> OTHER INFORMATION: probe for rat caspase 3 mRNA

<400> SEQUENCE: 4
ctggacaaca gttataaaat ggattatcct                                30

<210> SEQ ID NO 5
<211> LENGTH: 30
<212> TYPE: DNA
<213> ORGANISM: artificial sequence
<220> FEATURE:
<223> OTHER INFORMATION: probe for mouse caspase 3 mRNA

<400> SEQUENCE: 5
tattcaggcc tgccgtggat cagaactgga                                30

<210> SEQ ID NO 6
<211> LENGTH: 30
<212> TYPE: DNA
<213> ORGANISM: artificial sequence
<220> FEATURE:
<223> OTHER INFORMATION: probe for human caspase 3 mRNA

<400> SEQUENCE: 6
taaccgaaag gtggcaacag aatttgagtc                                30
```